United States Patent [19]

Piesch et al.

[11] 4,185,017

[45] Jan. 22, 1980

[54] N-SUBSTITUTED ε-CAPROLACTAMS

[75] Inventors: Steffen Piesch, Oberursel; Herbert Wille, Frankfurt am Main, both of Fed. Rep. of Germany

[73] Assignee: Cassella Aktiengesellschaft, Frankfurt, Fed. Rep. of Germany

[21] Appl. No.: 967,593

[22] Filed: Dec. 8, 1978

[30] Foreign Application Priority Data

Dec. 14, 1977 [DE] Fed. Rep. of Germany ....... 2755588

[51] Int. Cl.² .......................................... C07D 223/10
[52] U.S. Cl. ............................. 260/239.3 R; 525/398; 427/361; 427/370; 427/391; 427/393; 525/509
[58] Field of Search ................................. 260/239.3 R

[56] References Cited

U.S. PATENT DOCUMENTS 4,138,400  2/1979  Mitzlaff et al. ............... 260/239.3 R

*Primary Examiner*—Alan L. Rotman
*Assistant Examiner*—Robert T. Bond
*Attorney, Agent, or Firm*—Connolly and Hutz

[57] ABSTRACT

Condensation products of ε-caprolactam, formaldehyde and formamide, especially N-(formylaminomethyl)-ε-caprolactam and N-(N'-formyl-N'-hydroxymethylaminomethyl)-ε-caprolactam, are prepared by reacting formamide and formaldehyde in the presence of a base and in the presence or absence of ε-caprolactam at temperatures of 70° to 90° C. for 4 to 15 hours, then acidifying the reaction batch and, if no ε-caprolactam is present, adding ε-caprolactam, and distilling off water at 100° to 135° C.

The condensation products are valuable modifiers for use in the manufacture of aminoplast resins employed for impregnating paper and fabrics which are used for the manufacture of coated wood-based materials and laminates.

5 Claims, No Drawings

N-SUBSTITUTED ε-CAPROLACTAMS

The invention relates to condensation products of ε-caprolactam, formaldehyde and formamide, especially N-substituted ε-caprolactam compounds of the general formula

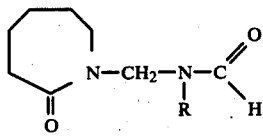

wherein R denotes hydrogen or —CH₂OH, and to processes for their preparation. The invention further relates to aminoplasts which contain the condensation products of ε-caprolactam, formaldehyde and formamide as a modifier, and to a process for the preparation of the modified aminoplasts.

According to the invention, the modified aminoplasts are outstandingly suitable for use as impregnating resins, for the impregnation of paper webs and fabric webs which are used for the manufacture of coated wood-based materials and laminates.

The condensation products are prepared from ε-caprolactam, formaldehyde and formamide. Advantageously, the reaction is carried out by first reacting the formamide with formaldehyde in the presence of a base, normally in the presence of an alkali metal hydroxide or alkali metal carbonate, for from 4 to 15 hours, advantageously whilst stirring, at temperatures of about 70° to 90° C. The reaction mixture is then acidified, for example by adding potassium sulphate, the ε-caprolactam is then added, the batch is subsequently heated to 100°–135° and the water formed during the condensation is distilled off. Advantageously, the water is distilled off azeotropically and/or under reduced pressure. For the azeotropic distillation, it is necessary to add an entraining agent, such as, for example, toluene, to the batch. For the distillation under reduced pressure it is possible to employ, for example, pressures of 10 to 500 mbar, especially 100 to 350 mbar. It is advantageous to select the reduced pressure so that the temperature of the reaction mixture does not exceed 135° C. The ε-caprolactam can also be employed from the very beginning of the reaction together with formaldehyde and formamide, but in that case only becomes involved in the reaction after the batch has been acidified.

The formaldehyde required is advantageously employed in the anhydrous form, that is to say, for example, as paraformaldehyde (polyoxymethylene) or trioxane. It is also possible to use gaseous formaldehyde. Very concentrated solutions of formaldehyde in organic solvents which are inert under the reaction conditions, or in water, can also be used. However, the use of solutions necessitates subsequently distilling off the solvent.

To prepare N-(formylaminomethyl)-ε-caprolactam of the formula Ia

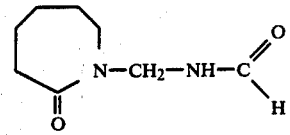

(R=H in formula I), the starting compounds are employed in the molar ratio of ε-caprolactam:formaldehyde:formamide=1:1:1. To prepare N-(N'-formyl-N'-hydroxymethylaminomethyl)-ε-caprolactam of the formula Ib

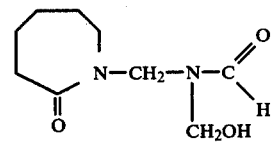

(R=—CH₂OH in formula I), the starting compounds are employed in the molar ratio of ε-caprolactam:formaldehyde:formamide=1:2:1.

After distilling off the water formed in the reactions, any entraining agent which may be present is distilled off. The compounds of the general formula I are obtained in the form of colourless oils, in virtually quantitative yield. The compounds of the formula Ia can be purified by vacuum distillation.

Compound Ib can also be prepared by methylolation of N-(formylaminomethyl)-ε-caprolactam of the formula Ia, or by reaction of bis-(hydroxymethyl)-formamide with ε-caprolactam. The crude products formed on preparation of the compounds of the general formula I can also be used for the modification of aminoplasts. Crude products of mixtures of compounds Ia and Ib are also suitable. The effectiveness of the compounds of the general formula I for modifying aminoplasts is so great that it suffices to prepare a mixture of the compounds of the general formula I with other reaction products of caprolactam and formaldehyde, or formaldehyde and formamide. Such mixtures have been obtained by carrying out the process mentioned for the preparation of the compound I but employing the starting materials in the molar ratio of ε-caprolactam:formaldehyde:formamide=1:a:b, wherein a is a number from 1 to 20 and b is a number from 1 to 19 and a and b are selected so that the quotient $(a/b+1)=0.5$ to 1. The numbers a and b need not necessarily be integers. The mixtures thus obtained can also be used in the form of their crude products for the modification of aminoplasts. The crude products are colourless oils which do not crystallise and are water-soluble. These aqueous solutions, like the aqueous solutions of the compounds of the general formula I, can also be used for modifying aminoplasts.

Aminoplasts include resinous products and their solutions which are formed by condensation of compounds containing amino or imino groups, namely the so-called aminoplast precursors, with carbonyl compounds, with or without a lower alkanol. The reaction between the aminoplast precursors, the carbonyl compounds and the alkanol, if any is used, is carried to the point that the products remain soluble and fusible. As soon as this state is reached, the condensation is discontinued, for example by cooling and adjusting the pH of the reaction mixture to a weakly alkaline value. The aminoplasts thus prepared, which are not fully condensed (and are also referred to as aminoplast precondensates) are used in the form of their aqueous solutions, especially as impregnating resins for the laminates industry, and for the surface improvement of wood-based materials.

In the surface improvement of wood-based materials, a decorative or protective layer is applied to wood fibreboard or wood chipboard by impregnating decorative paper or fabric webs with suitable aminoplasts, preferably melamine resins, and laminating these webs, having a certain residual moisture content, onto the sheets of the wood-based material by heat-curing. The pressure employed in the press can be about 10 to 100 bar (1 bar = $10^5 Pa \approx 1$ kg/cm$^2$) and the temperature can be 120° to 180° C. During the pressing process, the aminoplast cures completely and bonds the paper or fabric web to the sheet of the wood-based material. Laminates having a decorative or protective surface can be prepared similarly. In this case, the decorative web impregnated with aminoplast resin is pressed onto several layers of kraft paper, impregnated with phenolic resin, by heat-curing. The pressures used in the press are in this case in the range of about 50 to 150 bar, whilst the press temperatures are about 120° to 180° C., as for the decorative coating of wood-based materials. To increase the scratch resistance and abrasion resistance, a transparent paper impregnated with aminoplast resin, a so-called overlay paper, is placed on the decorative web before pressing. Occasionally, a barrier paper is also used between the decorative web and the core, and a peel-off paper is used on the back. Preferably, melamineformaldehyde resins are used for impregnating the overlay web and the decorative web. Overlay papers and barrier papers can also be used for the surface improvement of wood-based materials.

Coated wood-based materials and laminates are distinguished by their good chemical and physical properties. The non-elasticised aminoplasts used for impregnating the paper or fabric webs intended for the decorative or protective layer however only possess slight elasticity in the cured state, which is why surfaces produced with such resins tend to craze.

There has been no lack of attempts to overcome, or ameliorate, the insufficient elasticity of the decorative layer by employing additives in the impregnating resins. In particular, polyalcohols, sorbitol and sugars, as well as aromatic sulphonamides, have been proposed as additives. However, on adding polyalcohols or sugars, the water resistance of the cured resins becomes inadequate if the elasticity is to be sufficient. Sulphonamides alone do not suffice to achieve good elasticity.

On processing the aminoplasts, the soluble and fusible aminoplast precondensates are converted into infusible and insoluble products. During this curing, crosslinking occurs. However, even at the elevated processing temperatures the rate of this crosslinking reaction is insufficient for technological processes and must therefore be accelerated by adding so-called curing agents. Compounds which have an acidic reaction and/or eliminate acid are used as curing agents. Examples of such curing agents are ammonium salts or amine salts, for example ammonium chloride, ammonium thiocyanate, ethanolamine hydrochloride or strong organic acids, such as, for example, p-toluenesulphonic acid. When using free acids or salts having a strongly acid reaction, relatively short pot lives of the aminoplast resin result, which interferes with processing.

If caprolactam is added as a modifier to increase the elasticity of the finished surfaces, relatively large amounts of curing agent can be added to the impregnating resins and nevertheless a sufficiently long pot life before use can be achieved. However, unsatisfactory aspects are that the elasticity reserve is not very good, that the water resistance is reduced and that the surfaces obtained have an uneven gloss.

Impregnating resins which are suitable for the addition of large amounts of curing agent or of additives which accelerate curing, and are hence suitable for particularly rapid curing or processing are described, in the broadest sense of the word, as "short-cycle resins", and have, within a short time, gained a wide market.

It is known (German Document open for inspection 2,149,970) that the crazing of the surface of wood-based materials and laminates can be eliminated and that the elasticity of these materials can be increased if the paper or fabric webs intended for the decorative or protective layer are impregnated with an aminoplast resin modified with methylene-bis-formamide and are subsequently, in a manner known per se, laminated onto sheets of wood-based material, or processed to give a laminate. When using aminoplast resins modified with methylene-bis-formamide as so-called short-cycle resins, the finished surfaces also acquire a more uniform gloss. In practice it has been found, however, that on prolonged storage aminoplast resins modified with methylene-bis-formamide in part again lose their technological advantages, especially their resistance to crazing.

In the surface improvement of wood-based materials and the manufacture of laminates, satisfactory surfaces can be obtained, using an aminoplast resin of sufficient shelf life, if the paper or fabric web intended for the decorative or protective layer is impregnated with an aminoplast which is modified with a compound according to the invention and is subsequently, in a manner known per se, laminated to the sheet of wood-based material or converted to a paper laminate.

The aminoplast modified with a compound according to the invention normally contains, relative to the solids content of the finished resin, from 0.5 to 40% by weight, preferably from 2.5 to 15% by weight, of a compound of the general formula I or of a condensation product of ϵ-caprolactam:formaldehyde:formamide in the ratio of 1:a:b, wherein a represents a number from 1 to 20 and b represents a number from 1 to 19, and a and b are selected so that the quotient $(a/b+1) = 0.5$ to 1. In practice, the modification of the aminoplast with a compound according to the invention is carried out by condensing an aminoplast precursor, in a manner known per se, with a carbonyl compound, with or without further modifiers, such as water-soluble alcohols, and adding, before or during or after the condensation, a compound according to the invention or a condensation product of ϵ-caprolactam, formaldehyde and formamide having a molar ratio of ϵ-caprolactam:formaldehyde:formamide = 1:a:b, wherein a represents a number from 1 to 20 and b represents a number from 1 to 19 and a and b are selected so that the quotient $(a/b+1) = 0.5$ to 1, preferably 1:(1 to 2):1.

Suitable starting materials for the preparation of the aminoplasts are the known aminoplast precursors, such as, for example, urea, thiourea, dicyandiamide, guanamines, such as acetoguanamine or benzoguanamine, but especially melamine, and the carbonyl compounds known for use in condensation with aminoplast precursors, namely aliphatic and aromatic aldehydes and ketones, such as, for example, acetaldehyde, butyraldehyde, i-butyraldehyde, acetone, methyl ethyl ketone and the like, but especially formaldehyde. Mixtures of aminoplast precursors and/or of carbonyl compounds can also be used for the preparation of the aminoplast. Melamine-formaldehyde condensation products are particularly preferred, but co-condensates of formaldehyde, melamine and other aminoplast precursors, especially urea, as well as mixtures of malamine-formaldehyde condensates with condensation products of formaldehyde and other aminoplast precursors, especially urea, have also proved particularly suitable for the preparation of resins according to the invention.

The modifier can also be added in the form of aqueous solutions. If a condensation product of $\epsilon$-caprolactam:formaldehyde:formamide in the ratio of 1:1:1, or compound Ia, is used, the modifier is advantageously added towards the end of the condensation, but is best of all added to the cooled resin solution after completion of the condensation. It is also possible to add a part of the modifier from the beginning of the resin condensation and to add the remainder during or after the condensation. If a condensation product with a molar ratio of $\epsilon$-caprolactam:formaldehyde:formamide:=1:2:1, or the compound Ib, is used, it is advantageous first to prepare the condensation product of $\epsilon$-caprolactam, formaldehyde and formamide and to carry out the condensation of the resin after having subsequently added the aminoplast precursor and the carbonyl compound. If the condensation product of $\epsilon$-caprolactam:formaldehyde:formamide is added before or during the condensation of the resin, at least a part of the condensation product normally reacts with the resin precursors.

After completion of the aminoplast condensation, curing agents or curing accelerators, for example salts of weak to strong organic acids, for example diethanolamine acetate, ethanolamine hydrochloride, ethylenediamine acetate, ammonium thiocyanate, ammonium lactate or ethylenediamine phosphate, can also be added to the modified aminoplasts to accelerate the curing reaction, without thereby causing a deterioration of the elasticity of the coatings.

When preparing the resins, other modifiers can also be added, such as water soluble monoalcohols or dialcohols, for example methanol, ethanol, ethylene glycol and ethylene diglycol, as well as pentaerythritol, carbamates, such as, for example, methyl carbamate and methoxyethyl carbamate, salts of maleamic acid or fumaramic acid, sugars, sorbitol, salts of amidosulphonic acids, aromatic sulphonic acid amides and the like.

In preparing the resin the condensation is, as usual, taken only to a point where the resins still remain soluble and fusible. In carrying out this process, the condensation is as a rule taken until a particular limited dilutability with water is reached. In some cases, for example when adding substantial amounts of salts of amidosulphonic acid, the resins obtained may also be soluble in water in all proportions. To determine the water-dilutability, a sample of the resin is titrated with water at 20° C. For example, the statement "water-dilutability 1:X" means that 1 ml of resin at 20° C. can take up X ml of water without showing turbidity. Notes on how to carry out the condensation when preparing aminoplasts are to be found, for example, in Kirk-Othmer, Encyclopedia of Chemical Technology, 1st edition, vol 1 (1947), 756–759; Houben-Weyl "Methoden der organischen Chemie" ("Methods of organic Chemistry"), volume XIV/2, "Makromolekulare Stoffe" ("Macromolecular Materials"), part 2, 1963, Georg Thieme Verlag Stuttgart, especially pages 346 to 357 (urea condensates), pages 357 to 371 (melamine condensates), and pages 382 to 388 (condensation products of dicyandiamides and guanidine); John F. Blais "Amino Resins" Reinhold Publishing Corp., New York (1959), pages 26 to 53; C. P. Vale "Aminoplastics" Cleaver Hume Press Ltd., London (1950), pages 12 to 87; Ullmanns Encyklopadie der technischen Chemie (Ullmann's Encyclopedia of industrial Chemistry, 4th edition, volume 7 (1973), pages 403 to 414.

The manufacture of decoratively coated sheets of wood-based material, using the aminoplasts according to the invention, is carried out by impregnating the paper or fabric web with an aminoplast according to the invention, and processing it further in a manner known per se. Thus, the impregnated and dried paper or fabric web is pressed onto the prepared sheet of wood-based material under pressures of about 10 to 100 bar and at temperatures of about 120° to 180° C., advantageously using multi-daylight presses for the pressing operation. Analogously, if carrier webs impregnated with phenolic resins are employed instead of the sheets of wood-based materials, laminates can be produced, in which case press pressures of about 50 to 150 bar and temperatures of about 120° to 180° C. are employed.

Notes on the manufacture of coated sheets of wood-based material, and of laminates, are to be found in: John F. Blais, loc. cit., pages 122–138; C. P. Vale, loc. cit., pages 209–214, and Ullmann, loc. cit., pages 417–418.

The laminates and coated wood-based materials produced using the aminoplasts modified with the compounds according to the invention exhibit a high and uniform gloss, perfect curing and high elasticity and also conform to the other demands made of a perfect surface. The aminoplasts are stable on storage, that is to say the excellent results found on processing the aminoplasts are achieved over the entire life of the resin. Particularly good results are achieved when using the compound of the formula Ia for the preparation of aminoplasts. Very good results are also achieved when using the compound of the formula Ib. The compounds of the formula Ia and Ib can therefore also be employed in an impure form or in the form of mixtures, for example in the form of a condensation product of $\epsilon$-caprolactam:-formaldehyde:formamide in the ratio 1:1:1 or 1:2:1 or 1:(1 to 2):1. If $\epsilon$-caprolactam:formaldehyde:formamide are used in the ratio of 1:a:b to prepare the modifier, and more than 1 mol of formamide is used, mixtures are formed which contain the compounds of the formula Ia and/or Ib in addition to other reaction products, for example reaction products of formamide with formaldehyde, or of $\epsilon$-caprolactam with formaldehyde. Under suitable conditions, the mixture can, for example, also contain methylene-bis-formamide. In contrast to aminoplasts modified with methylene-bis-formamide, the aminoplasts modified with the compounds according to the invention or with the said mixtures retain their good properties over their entire life. The modified aminoplasts are also outstandingly suitable for use as short-cycle resins and in addition are also substantially insensitive to overcuring, as can occur in practice, for example due to prolonged press dwell times and/or increased press temperatures.

The high surface elasticity achieved in the laminates and coated wood-based materials manufactured using the modified aminoplasts mentioned above is, for example, responsible for the fact that on testing for crazing tendency according to DIN 53,799 of May 1975, item 4.7.1 (laminates) or 4.7.2 (coated wood-based materials), in which tests the samples are stored for 20 hours at 80° C., no crazing occurs. (This determination of the crazing tendency is hereinafter referred to as heat testing). Even on raising the temperature to 90° C. no crazing occurs in most cases. The compounds according to the invention, of the general formula I, and the condensation products of ε-caprolactam:formaldehyde:formamide in the ratio of 1:a:b, wherein a denotes a number from 1 to 20, b denotes a number from 1 to 19 and a and b are selected so that the quotient $a/b+1$ is 0.5 to 1, are substantially more stable to hydrolysis than is methylene-bis-formamide. The compounds according to the invention, of the general formula I, and the abovementioned condensation products, can be used in the form of oily crude products for the purpose of modifying aminoplasts, and such use facilitates metering and handling.

Unless stated otherwise, percentages quoted in the examples are percentages by weight; the temperature data are in °Centigrade.

EXAMPLE 1

ε-Caprolactam:formaldehyde:formamide = 1:1:1.

225 g of formamide, 2 g of KOH and 170 g of Granuform (90% strength by weight paraformaldehyde) are stirred for 10 hours at 80° C. 1.5 l of toluene, 560 g of ε-caprolactam and 6 g of $KHSO_4$ are then added and thereafter the water of reaction (about 95 g) is distilled off under normal pressure at a temperature of 120° C. The two layers initially formed gradually produce a clear solution. When no further water passes over, the toluene used as the entraining agent is distilled off. 820 g (representing 97% of theory) of a colourless oil remain; this oil is miscible with water in all proportions and can be used to modify aminoplasts.

Pure N-(formylaminomethyl)-ε-caprolactam can be obtained from the oil by distillation in a thin film evaporator; boiling point/1,064 mbar = 180-184° C. The pure N-(formylaminomethyl)-ε-caprolactam crystallises in long crystal needles and has a melting point of 48° C.

Analysis: calculated: C 57.1; H 7.1; N 16.7; found: C 57.3; H 7.0; N 16.4.

Instead of toluene, another entraining agent, for example xylene or ethylene chloride, can also be used.

EXAMPLE 2

Preparation of a modifier component with a molar ratio of ε-caprolactam:formaldehyde:formamide = 1:5:9.

695 g of formamide, 195 g of ε-caprolactam, 285 g of Granuform (90% strength by weight paraformaldehyde) and 1 g of KOH are stirred for 10 hours at 80° C., 4 g of $KHSO_4$ are then added and about 90 ml of water of reaction are distilled off at 100° C. under a pressure of 266.6 mbar. 950 g (80%) of a clear viscous liquid are obtained; this is miscible with water in all proportions and shows little tendency to crystallise, even in the undiluted state.

EXAMPLE 3

Preparation of a modifier component with a molar ratio of ε-caprolactam:formaldehyde:formamide = 1:10:19.

400 g of formamide, 60 g of ε-caprolactam, 165 g of Granuform (90% strength by weight paraformaldehyde) and 10 g of KOH are stirred for 6 hours at 80° C. 2.5 g of p-toluenesulphonic acid and 600 ml of toluene are then added and the water is distilled off azeotropically. When no further water passes over, the toluene is distilled off, ultimately under the vacuum from a waterpump. An oil which is miscible with water in all proportions is obtained in virtually quantitative yield.

It is possible to circumvent azeotropic distillation of the water if after the addition of the 2.5 g of p-toluenesulphonic acid, the mixture is fed continuously into a thin film evaporator in which it is caused to react, and the water is distilled off continuously, the conditions being a jacket temperature of 140° C. and a pressure of 333 mbar. The desired reaction product collects in the sump. With this procedure, again, the yield is virtually quantitative.

EXAMPLE 4

3,250 g of 39% strength by weight aqueous formaldehyde, 300 g of methanol, 250 g of water and 200 g of a 40% strength by weight aqueous solution of the sodium salt of amidosulphonic acid, 5 g of potassium hydroxide and 3,100 g of melamine are heated to 90° C. in the course of 30-40 minutes and are condensed at this temperature until the water-dilutability is 1:2.2 (duration about 4 hours). The pH value of the solution should be 10.0±0.2. After cooling to 50° C., this "basic resin" is mixed with 400 g of the condensation product prepared according to Example 2, to act as a modifier, and the mixture is brought to a solids content of 56% by weight with water. The content of the modifier of Example 2 in the resin is 8.4% by weight, calculated as solid relative to solid.

(4.1) 0.9% by weight, relative to solid resin, of the morpholine salt of para-toluenesulphonic acid is added to the above resin solution as a curing agent (this curing agent is also used in the examples which follow). A white decorative paper weighing 80 g/m² is impregnated with the impregnating liquor to which the curing agent has been added, until its final weight is about 200 g/m², and is then dried to a residual moisture content of 5.5-7% by weight (5 minutes/160° C.).

(The statement 5 minutes/160° C. means that to determine the volatile content a sample was stored for 5 minutes at 160° C. and the volatile content was calculated from the weight loss undergone during this storage).

(4.1.1) A part of the paper was subsequently pressed onto chipboard sheets on a short-cycle press under a pressure of 18 to 22 bar and at a temperature of 155° C. The press dwell time was 60 seconds. The surfaces of the coatings exhibited a uniform gloss, good degree of cure, and no crazing after heating at 140° C. for 20 hours.

(4.1.2) A part of the impregnated paper was pressed onto chipboard sheets on a short-cycle press under a pressure of 18 to 22 bar at a temperature of 180° C., with a dwell time of 3 minutes (which represents overcure pressing conditions). The surfaces of the coatings exhibited a uniform gloss, a very high degree of cure, and no crazing.

(4.1.3) A part of the impregnated paper was pressed onto chipboard sheets in a multi-daylight press under a pressure of 18 to 22 bar at a temperature of 140° C. The dwell time in the press was 10 minutes. The sheets were then cooled down again to a temperature of 70°-80° C. and released. The surfaces of the coated chipboard sheets exhibited very good degree of cure and a uniform high gloss, and showed no crazing after heating at 80° C. for 20 hours.

(4.2) 1.2% by weight of curing agent, relative to solid resin, were added to the resin solution of Example 4. A paper weighing 80 g/m² was impregnated in the impregnating liquor mixed with curing agent, and dried, as in Example 4.1. The impregnated papers were used in a press as in Example 4.1.2. The surfaces of the papers exhibited a uniform gloss, a very high degree of cure, and no crazing.

(4.3) The resin solution of Example 4 was stored, without addition of curing agent, for 14 days at room temperature (20°–25° C.), and 0.9% by weight of curing agent, relative to solid resin, was then added. A white paper weighing 80 g/m² was impregnated in this solution analogously to Example 4.1, and was used in a press as in Example 4.1.2. The surfaces of the coatings, which had a uniform gloss and showed a very high degree of cure, remained free from crazing.

(4.4) 0.4% by weight of curing agent was added to the resin solution of Example 4. After dilution with water to a concentration of about 52% by weight, a highly transparent overlay paper weighing about 30 g/m² and consisting of α-cellulose was impregnated in the solution to a final weight of 100–105 g/m² and dried to a volatile content of 6.5–7% by weight, and a decorative paper weighing 120 g/m² was impregnated to a final weight of 200–210 g/m² and dried to a volatile content of 5.5% by weight. A laminate was produced from the above together with soda kraft papers impregnated with phenolic resin. The stack consisted of:
1 overlay paper
1 decorative paper
9 kraft papers impregnated with phenolic resin
1 release film (siliconised paper).

The stack was pressed for 8 minutes at 140° C. under a pressure of 80 bar. Before release from the press, it was cooled down to 70°–80° C. The laminate sheet produced showed no crazing after heating for 20 hours at 80° C.

(4.5) Comparative Example.

The base resin described in Example 4 was mixed with 400 g of methylene-bis-formamide according to German Document open for inspection No. 2,194,979, and in other respects the procedure described in Example 4 was followed. 0.9% by weight of curing agent, relative to solid resin, was added to the resin solution obtained. A paper weighing 80 g was impregnated in this liquor analogously to Example 4.1, dried and used in a press analogously to Example 4.1.2. The surfaces of the coatings showed a uniform gloss and a very high degree of cure, and no crazing.

The resin solution was stored without added curing agent for 14 days at room temperature and was processed as above. The surfaces of the coatings showed isolated cracks over the entire surface.

(4.6) Comparative Example.

The preparation of the resin solution according to Example 4 was repeated, with the change that the modifier was omitted. Using the amino resin solution thus prepared, chipboard sheets were coated as in Example 4.1.2. The surfaces of the coated chipboards showed crazing over the entire surface.

EXAMPLE 5

490 g of the modifier of Example 2 were mixed into the base resin according to Example 4 (this amount corresponds to about 10% by weight, calculated as solid relative to solid). All other reaction conditions were kept constant. The impregnation was carried out as follows:

(5.1.1) 1.2% by weight of curing agent, relative to solid resin, were added to the resin solution of Example 5. A paper weighing 80 g was impregnated in this solution analogously to Example 4.1 and a part of the paper was pressed onto chipboard sheets as in Example 4.1.2. The surfaces of the coatings showed a uniform gloss, a very high degree of cure, and no crazing over the entire residual moisture range of 5 to 8% by weight.

(5.1.2) A second part of the paper was used for pressing onto the sheets in a short-cycle press at 180° C. under a pressure of 18 to 22 bar and with a dwell time of 5 minutes. Here again, the surfaces of the coatings showed a uniform gloss and a very high degree of cure, and no crazing over the residual moisture range of 5 to 8% by weight.

(5.2) 0.9% of curing agent was added to the resin solution of Example 5. A white paper weighing 80 g/m² was impregnated in this liquor analogously to Example 4.1, dried and pressed onto chipboard as in Example 4.1.3. The surfaces of the coated chipboard sheets showed very good degree of cure, a uniform and high gloss, and no crazing after heating for 20 hours at 80° C.

EXAMPLE 6

290 g of the modifier according to Example 2 were mixed into the base resin according to Example 4 (this amount corresponds to about 6% by weight, calculated as solid relative to solid). All other reaction conditions were kept constant.

(4.1) 0.9% of curing agent was added to the resin solution of Example 6 and processing was continued as in Example 4.1.2. The surfaces of the chipboards coated in this way remained free from crazing over the residual moisture range of 6 to 7% by weight.

(4.2) 0.4% of curing agent was added to the resin solution of Example 6 and processing was continued as in Example 4.1.3. The decoratively coated chipboard sheets thus produced also showed high gloss, a good degree of cure, and no crazing after heating for 20 hours at 80° C.

EXAMPLE 7

145 g of the modifier described in Example 2 were mixed into the base resin according to Example 4 (this amount corresponds to about 3% by weight, calculated as solid relative to solid), and 70 g of diethylene glycol were added. All the other conditions of Example 4 were kept constant.

(7.1) 0.4% of curing agent, relative to solid resin, was added to the resin solution of Example 7 and processing was continued analogously to Example 4.1.3. The surfaces of the chipboard sheets coated in this way exhibited a good degree of cure and high gloss, and remained free from crazing even after heating for 20 hours at 80° C.

EXAMPLE 8

380 g of aqueous 39% strength by weight formaldehyde solution, 10 g of ethylene glycol, 20 g of methanol, 10 g of sugar and 6 g of a 40% strength by weight solution of the sodium salt of amidosulphonic acid are brought to a pH value of 10.1 and 330 g of melamine are added whilst stirring. This mixture is heated to 90° C. and condensed until a water-dilutability of 1:1.5 is reached. After cooling the mixture to 50° C., 40 g of the modifier according to Example 2 and 150 g of water are added. The content of modifier according to Example 2 in the resin solution is 5.3% by weight, relative to solid resin. 0.4% of curing agent, relative to solid resin, is added to this resin solution. A decorative paper weighing 80 g/m² is impregnated in this solution as described in 4.1, and is pressed onto chipboard sheets analogously to 4.1.3. The surfaces of the chipboard coated in this way exhibit a good degree of cure and a uniform high gloss and remain free from crazing after heating for 20 hours at 80° C.

EXAMPLE 9

36.0 kg of an aqueous 39% strength by weight formaldehyde solution, 2.7 kg of diethylene glycol, 1.0 kg of methanol, 2.2 kg of the sodium salt of amidosulphonic acid, 3.7 kg of sugar and 15.0 kg of water are brought to a pH value of 10.1 with dimethylaminoethanol and 32 kg of melamine are added. This mixture is condensed at 90° C. until the water-dilutability is 1:2.0, and is cooled to 50° C., and 3 kg of the modifier according to Example 2 as well as 5 kg of water are added. The content of modifier according to Example 2 in the resin solution is 5.6% by weight, relative to solid resin.

(9.1) 0.9% by weight of curing agent, relative to solid resin, is added to the above resin solution. A paper weighing 80 g/m² is impregnated in the resulting resin solution analogously to 4.1 and chipboard sheets are coated with the impregnated paper analogously to 4.1.2. The surfaces of the coated sheets have a uniform gloss and a very high degree of cure, and remain free from crazing.

(9.2) 0.4% by weight of curing agent, relative to solid resin, was added to the resin solution of Example 9 and processing was continued analogously to Example 4.1.3. The surfaces of the chipboard sheets coated in this way exhibit a good degree of cure and uniform high gloss, and remain free from crazing after heating for 20 hours at 80° C.

EXAMPLE 10

3,200 g of formaldehyde (39% strength by weight aqueous solution), 400 g of water and 200 g of a 40% strength by weight aqueous solution of the sodium salt of amidosulphonic acid are brought to a pH value of 10.2 with 2 N NaOH and 3,100 g of melamine and 10 g of the modifier described in Example 2 are added. The mixture is then condensed at 90° C. until the water-dilutability reaches 1:4 and a further 200 g of the modifier are added. The mixture is condensed at 90° C. to a water-dilutability of 1:1.5 and is cooled to 50° C., and a further 150 g of the modifier are added. This resin is spray-dried, and the resulting product can be stored indefinitely. The technical performance properties are as described in Example 5.

EXAMPLE 11

500 g of the crude product obtained in Example 1 are stirred with 100 g of Granuform (90% strength by weight paraformaldehyde) and 0.4 g of potassium hydroxide for 10 hours at 80° C. An oil is obtained, which does not solidify even on prolonged standing, and which can be handled very easily. The yield is virtually quantitative.

Analysis: calculated: C 54.0; H 8.0; N 14.0; found: C 53.8; H 8.2; N 14.2.

Refractive index: 1.4995 at 20° C.

EXAMPLE 12

450 g of formamide, 630 g of Granuform (90% strength by weight paraformaldehyde) and 2 g of KOH are stirred at 80° C. for five hours. 1,130 g of ε-caprolactam and 8 g of potassium bisulphate are added to the resulting dimethylolformamide melt. The water of reaction is distilled off at an internal temperature of 120° C.±10° C. under a vacuum of 266 mbar, whilst stirring. The resulting product is identical with the product according to Example 11.

We claim:

1. A compound of the formula

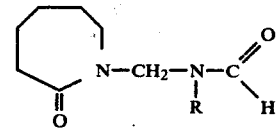

wherein
R is hydrogen or —CH₂OH.

2. N-(Formylaminomethyl)-ε-caprolactam.
3. N-(N'-Formyl-N'-hydroxymethyl-aminomethyl)-ε-caprolactam.
4. A crude product comprising a compound according to claim 1 obtained by condensing ε-caprolactam, formaldehyde and formamide in the molar ratio of 1:a:b, where a is a number from 1 to 20 and b is a number from 1 to 19 with the proviso that the quotient (a/b+1) is 0.5 to 1.
5. A process for the preparation of the compound according to claim 1 wherein formamide and formaldehyde are heated in the presence of a base, in the presence or absence of ε-caprolactam at temperatures of 70° to 90° C. for from 4 to 15 hours, acidifying the reaction batch, adding ε-caprolactam, if not previously present, and removing water at temperatures of 100° to 135° C.

* * * * *